(12) United States Patent
Maison et al.

(10) Patent No.: US 9,140,546 B2
(45) Date of Patent: Sep. 22, 2015

(54) APPARATUS AND METHOD FOR THREE DIMENSIONAL INSPECTION OF WAFER SAW MARKS

(75) Inventors: Benoit Maison, Wavre (BE); Andy Hill, San Jose, CA (US); Laurent Hermans, Borsbeek (BE); Frans Nijs, Leopoldsburg (BE); Karel Van Gils, Blanden (BE); Christophe Wouters, Balen (BE)

(73) Assignee: KLA-Tencor Corporation, Milpitas, CA (US)

( * ) Notice: Subject to any disclaimer, the term of this patent is extended or adjusted under 35 U.S.C. 154(b) by 542 days.

(21) Appl. No.: 13/376,391

(22) PCT Filed: Apr. 12, 2011

(86) PCT No.: PCT/IB2011/051572
§ 371 (c)(1),
(2), (4) Date: Jan. 30, 2012

(87) PCT Pub. No.: WO2012/014092
PCT Pub. Date: Feb. 2, 2012

(65) Prior Publication Data
US 2012/0300039 A1    Nov. 29, 2012

Related U.S. Application Data

(60) Provisional application No. 61/369,543, filed on Jul. 30, 2010.

(51) Int. Cl.
*G01B 11/25* (2006.01)
*G01N 21/95* (2006.01)
*H01L 21/66* (2006.01)

(52) U.S. Cl.
CPC ............ *G01B 11/25* (2013.01); *G01N 21/9501* (2013.01); *H01L 22/12* (2013.01); *G01B 2210/44* (2013.01)

(58) Field of Classification Search
None
See application file for complete search history.

(56) References Cited

U.S. PATENT DOCUMENTS

| | | | |
|---|---|---|---|
| 2001/0033386 A1 | 10/2001 | Kranz et al. | |
| 2008/0075353 A1 | 3/2008 | Tek et al. | |
| 2009/0050822 A1* | 2/2009 | Nakasuji et al. | 250/492.2 |
| 2009/0051930 A1 | 2/2009 | Moulin et al. | |

(Continued)

FOREIGN PATENT DOCUMENTS

| CN | 1182211 A | 5/1998 |
|---|---|---|
| CN | 1532518 A | 9/2004 |

(Continued)

*Primary Examiner* — William C Vaughn, Jr.
*Assistant Examiner* — Eileen Adams
(74) *Attorney, Agent, or Firm* — Suiter Swantz pc llo

(57) ABSTRACT

An apparatus (1) and a method for the three dimensional inspection of saw marks (2) on at least one surface (3) of a wafer (4) are disclosed. At least one camera (6) is required to capture an image of the entire surface (3) of the wafer (4). At least one line projector (8) provides a light bundle (5), centered about a central beam axis (9). The line projector (8) is arranged such that the central beam axis (9) is at an acute angle (α) with regard to the plane (P) of the wafer (4). A line shifter (12) is positioned in the light bundle (5) between each line projector (8) and the surface (3) of the wafer (4). A frame grabber (14) and an image processor (16) are used to synchronize and coordinate the image capture and the position of the pattern (20) of lines (22) on the front side (3F) and/or the back side (3B) of the wafer (4).

28 Claims, 11 Drawing Sheets

(56) References Cited

U.S. PATENT DOCUMENTS

| | | | |
|---|---|---|---|
| 2010/0073653 A1* | 3/2010 | Shibazaki | 355/53 |
| 2010/0239157 A1* | 9/2010 | O'Dell et al. | 382/145 |
| 2011/0235895 A1* | 9/2011 | Kitamura et al. | 382/144 |

FOREIGN PATENT DOCUMENTS

| | | |
|---|---|---|
| CN | 101171506 A | 4/2008 |
| CN | 101622525 A | 1/2010 |
| CN | 102192713 A | 9/2011 |
| DE | 10-2009-010837 A1 | 9/2010 |
| JP | S63-095344 A | 4/1988 |
| JP | 08-226899 A | 9/1996 |
| JP | 2000046743 A | 2/2000 |
| JP | 2001-124538 A | 5/2001 |
| JP | 2003527582 A | 9/2003 |
| JP | 2005345290 A | 12/2005 |
| JP | 2007-024873 A | 2/2007 |
| JP | 2008134196 A | 6/2008 |
| JP | 2009204343 A | 9/2009 |
| JP | 2010-117337 A | 5/2010 |
| JP | 2010117337 A | 5/2010 |
| JP | 2010522872 A | 7/2010 |
| JP | 2010181328 A | 8/2010 |
| WO | 0151887 A1 | 7/2001 |

* cited by examiner

APPARATUS AND METHOD FOR THREE DIMENSIONAL INSPECTION OF WAFER SAW MARKS

CROSS REFERENCE TO RELATED APPLICATIONS

This patent application claims priority of U.S. provisional patent application No. 61/369,543 filed Jul. 30, 2010, the application is incorporated herein by reference.

FIELD OF THE INVENTION

The present invention relates to an apparatus for the three dimensional inspection of saw marks on at least one surface of a wafer.

The invention relates as well to a method for determining saw marks on at least one surface of a wafer.

BACKGROUND OF THE INVENTION

Silicon wafers are used to manufacture photovoltaic cells. Each silicon wafer is cut from an ingot with a specialized saw. The surface of the wafers needs to be inspected for various defects. One type of defect is caused by the process of sawing-off the wafer from the silicon ingot. Saw grooves or saw marks are local, elongated, 3-dimensional departures from the normally flat surface of the wafer. Each saw mark is extended and formed in the sliding direction of the saw and parallel to said solar cell wafer in the surface of said solar cell wafer. In case of a cylindrical shaped ingot the saw marks run in the same direction as the saw is operated. In case of a cubical ingot the saw marks are almost parallel to one edge of the wafer. The length of the saw marks may vary between a few centimeters and the entire width of the wafer. Additionally, also the width and depth of the saw marks may vary. The form and status of a saw mark in a solar cell wafer influences the quality of the solar cell wafer.

Japanese patent application JP 2010-181328 A discloses a test equipment for a solar cell wafer surface which inspects a formation state of a saw mark in the surface of the solar cell wafer. The solar cell wafer being the subject of examination is conveyed by a conveyor in a direction parallel to the longitudinal direction of a saw mark formed in the surface. The test equipment is provided with a floodlight, a camera and a computer. The floodlight is arranged at an oblique direction to the surface and is adapted for lighting a sub-division to the surface of said solar cell wafer. The lighting direction perpendicularly intersects the longitudinal direction of the saw mark. The floodlight is a halogen lamp, a fluorescent lamp, etc., for example. A diffusion plate is used to diffuse the light for irradiating said solar cell wafer. The camera generates data of the picture of the surface of said solar cell wafer. The imaging direction (optical axis direction) of said camera may be an oblique direction to the surface of said solar cell wafer.

Japanese patent application JP 2008-134196 A discloses a technology wherein the picture of the surface of the solar cell wafer has dispersion in the light and darkness according to the grain boundary which exists in the solar cell wafer. In the picture of the surface of a solar, cell wafer, the brightness of the image of said saw mark is relatively low. Therefore, the image of said saw mark cannot be exactly identified as a candidate of a defect.

Japanese patent application JP 2005-345290 A discloses a technology, whereby a pixel of a predetermined number with high brightness is extracted from a division picture. In many cases, the problem is that an image of a saw mark cannot be exactly extracted from a picture of the surface of a solar cell wafer as a candidate for a defect. Therefore, it is difficult to set up a predetermined region centering on said pixel which distinguishes one image of said saw mark at a time.

The Japanese patent application JP 2000-046743 A applies inspection light to a wafer where recesses and projections in a specific direction are formed in parallel from a specific direction. A plurality of LEDs is arranged in a semi-circular shape, and a lighting direction is controlled by a lighting-controlling device. The lighting-controlling device sets a lighting direction in the initial state of a wafer on a turntable and successively adjusts the lighting direction for an angle based on a rotary angle signal from the encoder of the turntable. Cameras pick up the image of the edge part of the wafer every time the turntable stops at a specific angle. An image-processing device picks up an image from the cameras and detects a defect by image processing.

The German patent application DE 10 2009 010 837 A1 discloses a method for inspecting for the existence of sawing grooves on wafers utilized for manufacturing solar cells. The method involves projecting a light line on a wafer by a laser light source, and transporting the wafer on a transport device. The wafer is inspected during continuous transport of the wafer, where the wafer is arranged on the transport device such that sawing grooves are aligned at a right-angle to a transportation direction. A partial region of the wafer is examined such that images of the partial region are recorded using a surface camera.

The prior art methods show drawbacks. The manual methods are slow and do not inspect all solar cell wafers. As a result there is an insufficient detection of the defect (saw mark). Furthermore, many prior art methods are less accurate and less repeatable.

Some of the prior art methods only inspect part of the solar cell wafer, whereas saw grooves or saw marks can be present anywhere on the wafer. Particularly, also the deepest part of the saw groove can be anywhere on the wafer, too. As a consequence, the prior art methods may miss a groove completely or underestimate its depth. This also results in an insufficient detection of the defect.

There are some prior art methods which inspect the solar cell wafers in one direction only. However, the wafers are on a moving belt, and consequently, grooves perpendicular to the direction of transport of the belt can be detected and measured. In order to provide a sufficient detection these methods require operators knowing the direction in which the previous sawing process occurred. All wafers need to be placed in the same orientation onto the moving belt. As a consequence, the inspection process is slower, more error-prone, and less flexible.

SUMMARY OF THE INVENTION

The object of the invention is to create an apparatus which provides an automatic, fast and reliable three dimensional inspection of the entire front side and/or the entire back side of a wafer with regard to saw grooves or saw marks.

This object is achieved by an apparatus for three dimensional inspection of saw marks on at least one surface of a wafer comprising:
- at least one camera defining a field of view and being arranged to image a plane of the wafer, wherein the field of view is designed such that at least a portion of a surface of the wafer is captured;
- at least one line projector providing a light bundle centered about a central beam axis, wherein the at least one line projector is arranged such that the central beam axis is arranged at an acute angle with regard to the plane of the wafer, and wherein the at least one line projector is provided with light from at least one light source and is adapted to project a pattern of a plurality of lines onto a front side and/or a back side of the wafer and thereby covering at least a portion of the surface of the front side or the back side of the wafer;

at least one line shifter being positioned in the light bundle between the line projector and the surface of the wafer; and a frame grabber and an image processor, wherein image capture of the front side or the back side of the wafer is synchronized by the frame grabber in coordination with the position of the pattern of lines on the front side and/or the back side of the wafer.

It is a further object of the invention to create a method which provides an automatic, fast and reliable three dimensional inspection of the entire front side and/or the back side of wafers with regard to saw grooves or saw marks.

The above object is achieved by a method for determining saw marks or saw grooves on at least one surface of a wafer, comprising the steps of:

providing at least one line projector;

projecting a first pattern of lines of a first orientation onto the at least one surface of the wafer;

capturing a first set of first images of the surface of the wafer, wherein for each image of the first pattern of lines the lines are shifted a definite distance perpendicular to the orientation of the first pattern of lines;

projecting a second pattern of lines of a second orientation onto the surface of the wafer;

capturing a second set of second images of the surface of the wafer, wherein for each image of the second pattern of lines the lines are shifted a definite distance perpendicular to the second orientation of the second pattern of lines;

generating a combined first image from the set of first images and generating a combined second image from the set of second images, and thereby computing an improved set of first images from the combined first image and an improved set of second images from the combined second image;

detecting grooves in at least one of the improved set of first images and in at least one of the improved set of second images;

measuring a depth of a detected groove in at least one image of the improved set of first images or improved set of second images;

averaging the depth of the grooves across the images of the improved set of first images and the images of the improved set of second images; and documenting the depth and the location and the orientation of the detected grooves on the surface of the wafer.

In case a second pattern of lines is projected in a second orientation onto the surface of the wafer, a second set of second images of the surface of the wafer is captured, wherein for each image of the second pattern of lines the lines are shifted a definite distance perpendicular to the second orientation of the second pattern of lines. The first pattern of lines may be identical to second pattern of lines. The only difference is that the first pattern of lines is not parallel to the second pattern of lines.

In one embodiment of the inventive apparatus one camera is provided. The camera defines a field of view and is arranged perpendicular to a plane of the wafer. The field of view of the camera is designed such that the entire surface of the wafer is or at least a portion of the surface of the wafer is captured. One line projector is sufficient in case the orientation of the saw grooves on the surface of the wafer is known. In case only a single line projector is used, a loading device is required which loads the wafers in a defined orientation so that the saw grooves are not parallel to the pattern of lines projected onto the surface of the wafer. The line projector projects a light bundle which is centered about a central beam axis on to the surface of the wafer. The line projector is arranged such that the central beam axis is arranged at an acute angle with regard to the plane of the wafer. A light source provides light to the line projector. The line projector is adapted to illuminate a front side or a back side of the wafer with a pattern of lines and thereby covering the complete surface of the front side or the back side of the wafer. A line shifter is positioned in the light bundle between the line projector and the surface of the wafer. A frame grabber and an image processor coordinate and synchronize the image capture of the front side or the back side of the wafer, wherein the frame grabber coordinates the position of the pattern of lines on the front side or the back side of the wafer.

In another embodiment of the inventive apparatus a first line projector and a second line projector are provided. The first line projector is arranged such that the central beam axis is arranged at an acute angle with regard to the plane of the wafer. In addition, the first line projector is adapted to project a pattern of a plurality of lines in a first orientation onto a front side or a back side of the wafer and thereby covering the complete surface of the front side or the back side of the wafer. The second line projector provides a light bundle centered about the central beam axis. In addition, the second line projector is arranged such that the central beam axis is arranged at an acute angle with regard to the plane of the wafer. The second line projector is provided with light from a light source and is adapted to project a pattern of a plurality of lines in a second orientation onto the front side or the back side of the wafer and thereby covering the complete surface of the front side or the back side of the wafer. The first and the second line projector project the first and second pattern of a plurality of lines in the same surface of the wafer. The surface of the wafer is the front side or the back side respectively. A line shifter is positioned in each light bundle between the first and second line projectors respectively and the surface of the wafer. This arrangement of the first and second line projectors is advantageous if there is no information available about the orientation of the saw grooves or saw marks on the surface of the wafer.

A further embodiment of the invention enables to simultaneously capture the front side and the back side of the wafer. The inventive apparatus comprises two cameras. Each camera defines a field of view and is arranged perpendicular to a plane of the front side of the wafer and the back side of the wafer. The field of view of the two cameras is designed such that the entire front side and the entire back side respectively of the wafer is captured. At least one first line projector provides a light bundle which is centered about a central beam axis, wherein the first line projector is arranged such that the central beam axis is arranged at an acute angle with regard to the plane and the front side respectively of the wafer. At least one second line projector provides a light bundle which is centered about a central beam axis, wherein the second line projector is arranged such that the central beam axis is arranged at an acute angle with regard to the plane and the back side of the wafer respectively. A line shifter is positioned in the light bundle between each line projector and the surface of the wafer.

Moving means may be provided for enabling a relative rotation between the wafer and the at least one line projector.

The relative rotation is such that the acute angle of the at least one line projector with regard to the plane of the wafer is maintained. With the moving means it is possible to project a second pattern of a plurality of lines in a second orientation onto the surface of the wafer. Preferably, the lines of the first pattern of lines are perpendicular to the lines of the second pattern of lines. According to one embodiment, the moving means rotates the wafer so that the first pattern of lines and the second pattern of lines can be projected one after the other onto the surface of the wafer. Another possibility is that the line projector is pivoted with respect to the surface of the wafer, in a first orientation the line projector projects a first pattern of lines and in a second orientation the line projector projects a second pattern of lines onto the surface of the wafer. The frame grabber and the image processor synchronize the image capture of the first pattern of lines and the second pattern of lines projected onto the surfaces of the wafer, the position of the line shifter in the light bundle and the relative rotational position of the wafer and the line projector with respect to each other.

A further embodiment of the invention is designed such that the apparatus for three dimensional inspection of saw marks has at least one camera defining a field of view and being arranged to image a plane of the wafer, wherein the field of view is designed such that at least a portion of a surface of the wafer is captured. Means for loading the wafer are provided such that the saw marks are in a defined orientation in the field of view of the camera. At least one line projector provides a light bundle centered about a central beam axis, wherein the at least one line projector is arranged such that the central beam axis is arranged at an acute angle with regard to the plane of the wafer, and wherein the at least one line projector is provided with light from at least one light source and is adapted to project a pattern of a plurality of lines onto a front side and/or a back side of the wafer and thereby covering at least a portion of the surface of the front side or the back side of the wafer. At least one line shifter is positioned in the light bundle between the line projector and the surface of the wafer. The frame grabber and the image processor are required to capture the image of the front side or the back side of the wafer. Additionally, the frame grabber is triggered in order to coordinate the position of the pattern of lines on the front side and/or the back side of the wafer. The means for loading the wafer can be used to load the wafer in a different orientation in order to capture the images of the wafer in a second orientation of the saw marks.

A further embodiment of a method of the present invention is that the orientation of the saw marks needs to be determined so that the wafer can be loaded into the apparatus in a defined orientation. Only one projector is needed in order to detect saw marks on a surface of a wafer. A line projector projects a pattern of a plurality of lines onto a front side or a back side of the wafer and thereby covering at least a portion of the surface of the front side or the back side of the wafer. The pattern of lines is oriented at an angle (not parallel) with respect to the saw marks. In a preferred embodiment the lines are oriented approximately perpendicular to the saw marks. A first set of first images of the surface of the wafer is captured, wherein for each image of the first pattern of lines the lines is shifted a definite distance perpendicular to the orientation of the first pattern of lines. A combined first image from the set of first images is generated, and thereby computing an improved set of first images from the combined first image. Grooves are detected in at least one of the improved set of first images. Finally an averaging and documenting step is carried out.

The first pattern of lines is oriented at an angle with respect to the saw marks, Most preferably, the first pattern of lines is perpendicular to the saw marks on the front side or the back side of the wafer respectively.

The at least one line shifter can be a glass plate which is connected to a motor for rotating the glass plate so that the first or second pattern of lines is shifted on the surface of the wafer. According to another embodiment, the at least one line shifter has a plurality of glass plates, whereby each glass plate is arranged at a different angle in a positioner. The positioner is drivable by a motor in order to bring a glass plate with a specific tilt angle into the light bundle. The differences in the tilt angles cause the first or second pattern lines to shift on the surface of the wafer.

In an embodiment, each of the at least one line projectors of the apparatus has two patterned glass plates with a pattern of lines arranged between an exit lens and a condenser system of the at least one line projector. A first glass plate has a variable-pitch Ronchi ruling in order to compensate for a perspective effect and to project the uniform pattern of lines onto the surface of the wafer. The second glass plate has a variable transmittance pattern to compensate for a perspective effect and to project the pattern of lines of uniform brightness onto the surface of the wafer.

In an embodiment, the light source is directly attached to the at least one line projector. According to another embodiment, the light is delivered from the at least one light source to the at least one line projector via light guides. The at least one light source may comprise high brightness LEDs.

According to a preferred embodiment two line projectors are arranged such that the central beam axis of a first line projector is parallel to the X-direction and the central beam axis of a second line projector is parallel to the Y-direction. In other words, the two line projectors enclose an angle of 90° with respect to the X- and V-directions of a Cartesian coordinate system. The respective central beam axis of each line projector encloses an angle of 18° with the plane of the wafer (horizontal plane). The camera is looking down vertically and three images are captured by the camera. The first set of images is captured whilst the first line projector is illuminated. A motor tilts a 2 mm thick glass plate in front of each line projector. The tilt angles are −4.44°, 0° and 4.44° relative to the respective perpendicular central beam axis of the respective line shifter. For each tilt angle an image is captured. The captured images are combined in order to remove unwanted artifacts. Image processing methods look for and measure saw marks or saw grooves in each set of the three images.

According to a preferred embodiment of a method of the present invention the orientation of the saw marks is known a priori, for example from a preceding inspection step. At least one camera and at least two line projectors are needed in order to detect saw marks/grooves on a wafer. Each line projector can project a pattern of a plurality of lines onto a front side or a back side of the wafer and thereby covering at least a portion of the surface of the front side or the back side of the wafer. The patterns of lines of the line projectors are under an angle with respect to each other, meaning the patterns of lines of the line projectors are not parallel but of different orientations. In a preferred embodiment consisting of two line projectors the two patterns of lines of the line projectors are approximately perpendicular to each other. Additionally at least one of the patterns of lines is oriented at an angle with respect to the saw marks. In a preferred embodiment the lines of one projector are oriented approximately perpendicular to the saw marks. The a priori information about the orientation of the saw marks is used to select the line projector that projects the line pattern that is closest to perpendicular to the saw marks. This line project is used during image capture to project line patterns. A first set of first images of the surface of the wafer is captured, wherein for each image of the first pattern of lines the lines are shifted a definite distance perpendicular to the orientation of the first pattern of lines. A combined first image from the set of first images is generated, and thereby computing an improved set of first images from the combined first image. Grooves are detected in at least one of the improved set of first images. Finally an averaging and documenting step is carried out. (The advantage of this embodiment is that throughput can be higher because image capture time is minimized).

Finally, the apparatus reports the position and depth of the deepest saw marks detected. The saw grooves or saw marks are measured in pixels by estimating the position of each line on either side of the saw groove by means of curve fitting. The differences between the two sides are computed by averaging over a certain distance along the groove. A calibration model is used to translate depth measured in pixel to depth expressed in actual distance units. The calibration model takes into account the perspective and other distortion caused by the line projectors and the camera.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

Figure 1:
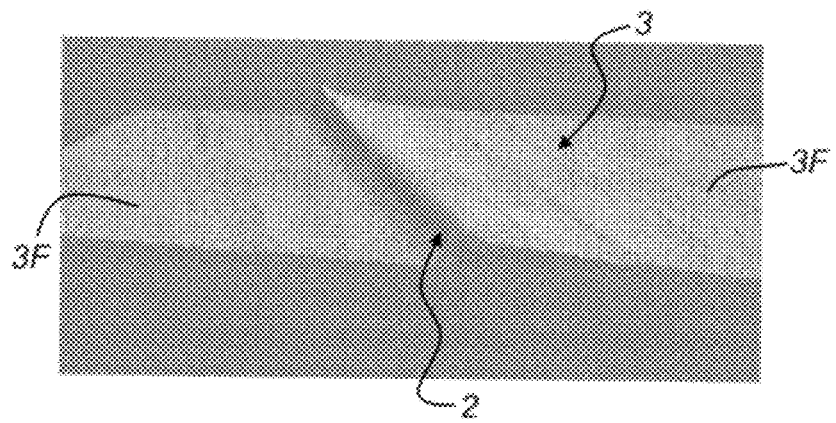
FIG. 1 shows a part of a saw groove which has a step-like shape in an image taken with a confocal microscope.

Same reference numerals refer to same elements throughout the various figures. Furthermore, only reference numerals necessary for the description of the respective figure are shown in the figures. The shown embodiments represent only examples of how the apparatus and method according to the invention can be designed. This should not be regarded as limiting the invention.

FIG. 1 shows a partial view of a saw groove on the front side 3F of a wafer 4 (see FIG. 2), wherein the saw groove 2 has a step-like shape. Silicon wafers used to manufacture photovoltaic cells need to be inspected for various defects. One type of defect is caused by the process of sawing-off the wafer from a silicon ingot (not shown). The form of the silicon ingot can be a cuboid or a cylinder. Consequently, wafer 4 is round or rectangular, respectively. Saw grooves 2 or saw marks are local, elongated and 3-dimensional departures from the normally flat front side 3F or back side 3B of wafer 4. In case wafer 4 is rectangular the saw grooves 2 run almost parallel to the edge of wafer 4, in the same direction as the saw, and their length can vary between a few centimeters and the entire width of wafer 4. The width of saw grooves 2 and their depth can also vary.

Figure 2:
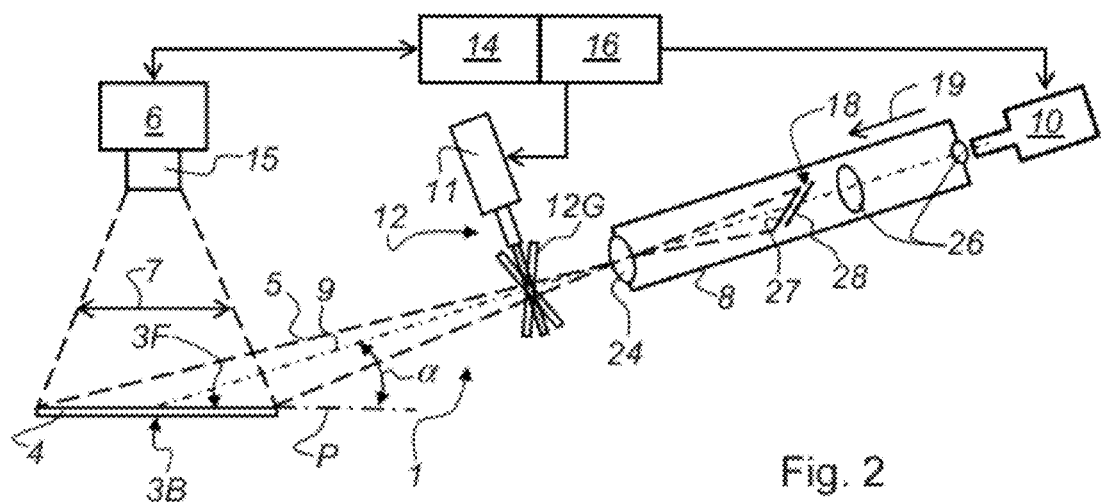
FIG. 2 shows a schematic side view of an embodiment of an apparatus for three dimensional inspection of wafer saw marks, wherein at least one line projector is used.

FIG. 2 shows a schematic side view of an embodiment of the inventive apparatus 1 for the three dimensional inspection of saw marks 2 on at least one surface 3 of wafer 4. The surface 3 of wafer 4 is the front side 3F or the back side 3B of wafer 4. Surface 3 of wafer 4 is imaged by a camera 6 defining a field of view 7 and being arranged perpendicular to a plane P of wafer 4. The optical system 15 of camera 6 is designed such that next to defining the field of view 7 also the entire surface 3 of wafer 4 is captured by a sensor (not shown) of camera 6. The sensor can be an area sensor or can work according to a line scan principle. It is important that the sensor needs to be sensitive to the wavebands of the illumination provided by the at least one line projector.

Apparatus 1 has a line projector 8 providing a light bundle 5 centered about a central beam axis 9. The entire surface 3 of wafer 4 is illuminated with the light bundle 5 by the line projector 8. Line projector 8 is arranged with respect to the surface 3 of wafer 4 such that the central beam axis 9 is arranged at an acute angle a with regard to the plane P of wafer 4. A light source 10 is attached to the line projector 8 and provides the light in order to form the light bundle 5 for the illumination of the surface 3 of wafer 4. Light source 10 is preferably based on high brightness LEDs.

The line projector 8 has condenser lenses 26 which are arranged in a propagation direction 19 of the light prior to two patterned glass plates 18. With the patterned glass plates 18 a pattern 20 of a plurality of lines 22 (see FIGS. 7A to 9B) is created in the light bundle 5. Line projector 8 has an exit lens 24 in order to project the pattern 20 of lines 22 onto a front side 3F and/or a back side 3B of wafer 4. The two patterned glass plates 18 are arranged between the exit lens 24 and the condenser lenses 26. A first glass plate 27 of the two patterned glass plates 18 has a variable-pitch Ronchi ruling in order to compensate for a perspective effect and to project the uniform pattern 20 of lines 22 onto the surface 3 of wafer 4. A second glass plate 28 of the two patterned glass plates 18 has a variable transmittance pattern to compensate for a perspective effect and to project the pattern of lines 22 of uniform brightness onto the surface 3 of wafer 4.

At least one line shifter 12 is also positioned in the light bundle 5 between the line projector 8 and the surface 3 of wafer 4. The embodiment of the line shifter 12 as disclosed in FIG. 2 is a glass plate 12G which is connected to a motor 11. The motor 11 rotates the glass plate 12G so that the first or second pattern 20 of lines 22 is shifted on the surface 3 of wafer 4. FIG. 2 shows three different angle positions of the glass plate 12G. With the different angle positions it is possible to shift the pattern 20 of lines 22 over the surface 3 of wafer 4. In an alternative embodiment (not shown) of the line shifter 12 a plurality of glass plates 12G is mounted in a positioner. Each glass plate 12G is arranged at a different angle and the positioner is drivable by a motor in order to bring a glass plate 12G of a specific tilt angle into the light bundle 5 so that the lines first or second pattern 20 are shifted on the surface 3 of wafer 4.

Line shifter 12 may comprise as well several glass plates 12G which have the same tilt angle but differ in thickness. In order to achieve the shifting of the pattern 20 of lines 22 over the surface 3 of wafer 4, prior to capturing an image a single specific glass plate 12G is brought into light bundle 5 between line projector 8 and surface 3 of wafer 4.

The image capture with the camera 6 is synchronized with the motor 11 of the line shifter 12 and the power supply to light source 10. A frame grabber 14 and an image processor 16 are electrically connected with the camera. The image capture of the front side 3F or the back side 3B of wafer 4 is synchronized by the frame grabber 14 in coordination with the position of the pattern 20 of lines 22 on the front side 3F and/or the back side 3B of wafer 4.

In case the orientation of the saw grooves 2 on the surface 3 of wafer 4 is known, apparatus 1 can operate with a single line projector 8. Without prior knowledge of the orientation of the saw grooves 2 it is necessary to project two patterns 20 of lines 22 at two different orientations onto the surface 3 of wafer 4. Preferably, both patterns 20 are perpendicular to one another. This can be achieved by a first line projector $8_1$ and a second line projector $8_2$ which are arranged such that the lines 22 of the two patterns 20 of lines 22 on the surface 3 of wafer 4 are perpendicular to one another (see FIGS. 7A to 9B).

In an alternative solution a relative rotational motion is carried out the between the single line projector 8 and the surface 3 of wafer 4. The first set of images is captured with the pattern 20 of lines 2 in a first orientation and the second set of images is captured in a second orientation after a respective relative rotational motion.

Figure 3:
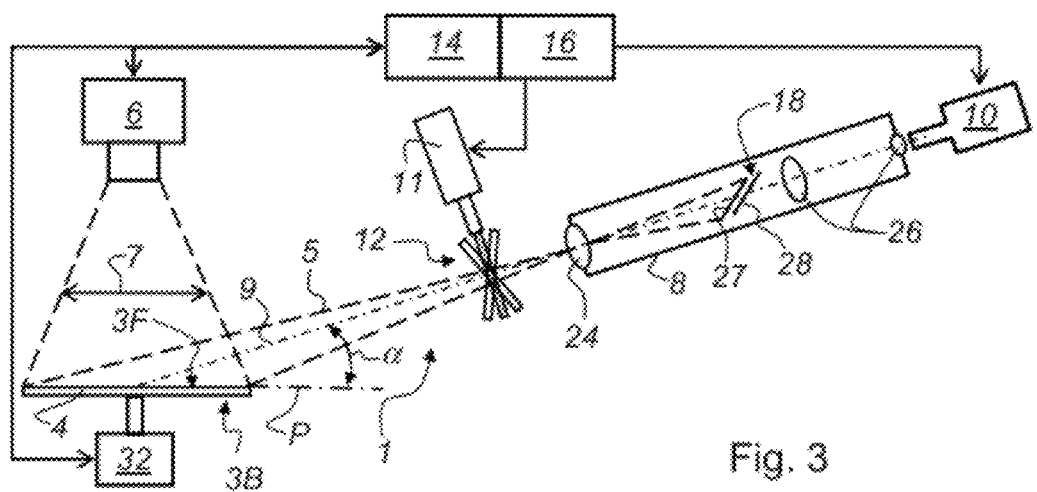
FIG. 3 shows a schematic side view of another embodiment of the apparatus for the three dimensional inspection of wafer saw marks, wherein means for carrying out a relative rotational motion between the wafer and the single line projector are provided so that the wafer surface can be illuminated in two different orientations.

FIG. 3 shows an alternative embodiment of the invention. Each wafer 4 to be inspected is transported in plane P until it reaches an inspection position, i. e., is in the field of view 7 of camera 6, where wafer 4 is illuminated by light bundle 5 of the line projector 8. The wafer 4 reaches the inspection position in an initial orientation. As mentioned above, the pattern 20 of lines 22 (see FIG. 7A to 9B) is moved by the line shifter 12 across the surface 3 of wafer 4 to be inspected by apparatus 1. Moving means 32 (see FIG. 3) provide a relative rotation between the wafer 4 and the line projector 8. During the relative rotation the acute angle α of the line projector 8 with regard to the plane P of wafer 4 is maintained. The relative rotation is necessary in order to project a second pattern 20 of a plurality of lines 22 in a second orientation onto the surface 3 of wafer 4.

According to the method of operation of the embodiment disclosed in FIG. 3, camera 6 captures a plurality of images from the surface 3 of wafer 4. The line shifter 12 enables that the images differ from each other by a fraction of the pitch of the pattern 20 of lines 22 projected onto the surface 3 of wafer. The lines 22 partly overlap between the images. Once the multiple images are captured, the moving means 32 carry out the relative rotation between the wafer 4 and the line shifter 12. In a preferred mode of operation, wafer 4 is rotated by the moving means 32. The degree of rotation is preferably 90°. After completing the rotation, camera 6 captures an additional set of images, wherein the line projector 8 projects a second pattern 20 of lines 22 onto the surface 3 of wafer 4, wherein the second pattern 20 of lines 22 is oriented at an angle with respect to the first pattern 20 of lines 22. In case the degree of rotation is 90° the first pattern 20 of lines 22 is oriented at 90° with respect to the second 20 pattern of lines 22. The camera 6, the moving means 32, the motor 11 of the line shifter 12 and the light source 10 are coordinated by the frame grabber 14 and the image processor 16.

Figure 4:
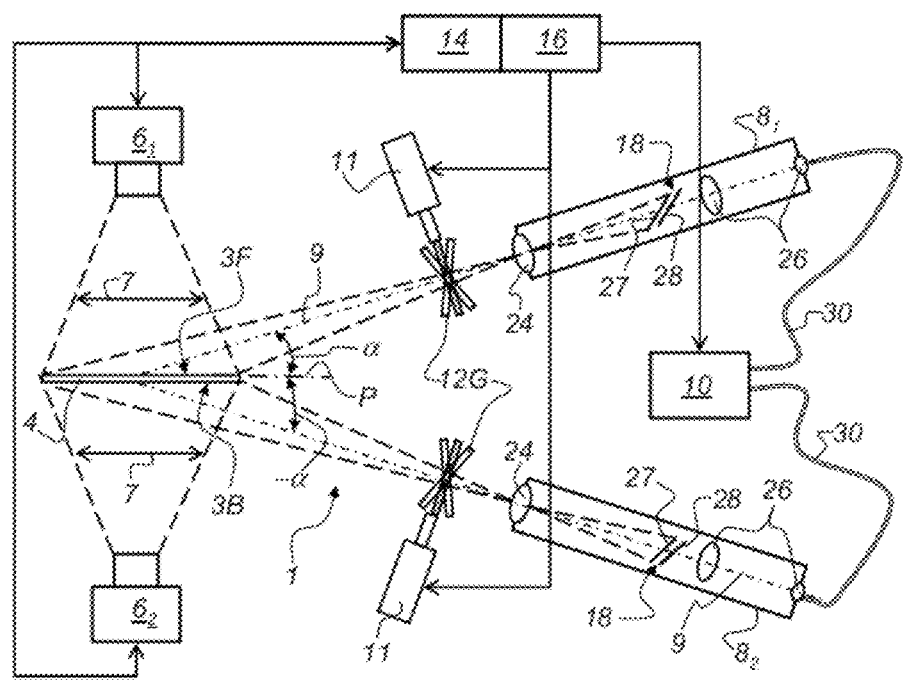
FIG. 4 shows a schematic side view of the apparatus for the three dimensional inspection of wafer saw marks, wherein according to this embodiment the front side and the back side of the wafer are inspected simultaneously by at least two line projectors.

FIG. 4 shows an embodiment of the invention with a first line projector $8_1$ and a second line projector $8_2$. The first line projector $8_1$ is adapted to project a pattern 20 of lines 22 onto the front side 3F of wafer 4. The second line projector $8_2$ is adapted to project a pattern 20 of lines 22 onto the back side 3B of wafer 4. A first camera $6_1$ is arranged opposite to the front side 3F of wafer 4 and a second camera $6_2$ is arranged opposite to the back side 3B of wafer 4. With the arrangement disclosed in FIG. 4 it is possible to simultaneously capture multiple images of the front side 3F of wafer 4 and of the back side 3B of wafer 4. In this embodiment the light to the line projectors $8_1$, $8_2$ is provided by a single light source 10 via individual light guides 30.

The embodiments of the apparatus 1 disclosed in FIGS. 2 to 4 are exemplary embodiments and should not be considered as a limitation of the invention. A skilled person in the art would consider as well an apparatus 1 with a first line projector $8_1$, a second line projector $8_2$, a third line projector $8_3$ (not shown) and a fourth line projector $8_4$ (not shown). In this embodiment the first line projector $8_1$ and the third line projector $8_3$ are arranged such that they project the respective pattern 20 of lines 22 at 0° and 90° degrees respectively onto the front side 3F of wafer 4. The second line projector $8_2$ and the fourth line projector $8_4$ are arranged such that they project the respective pattern 20 of lines 0° and 90° degrees respectively onto the back side 3B of wafer 4. In order to speed up image capture it is possible to use different wavebands for each line projector $8_1$, $8_2$, $8_3$ or $8_4$. At least one color sensitive camera or a camera with filters is required to capture the images.

In a further embodiment (not shown) a first line projector $8_1$ and a second line projector $8_2$ are arranged such that they project the respective pattern 20 of lines 22 at 0° and 90° degrees respectively onto the front side 3F of wafer 4.

The wafers 4 to be inspected rest on a belt (not shown) which transports the wafers 4 into the inspection position, i.e., into the field of view 7 of the camera 6. It is possible to inspect the front side 3F of the wafer 4. As disclosed in FIG. 4 the front side 3F and the back side 3B of the wafer 4 can be inspected simultaneously while the wafer 4 is held by a vacuum pick-up gear (not shown) or any equivalent.

Figure 5:
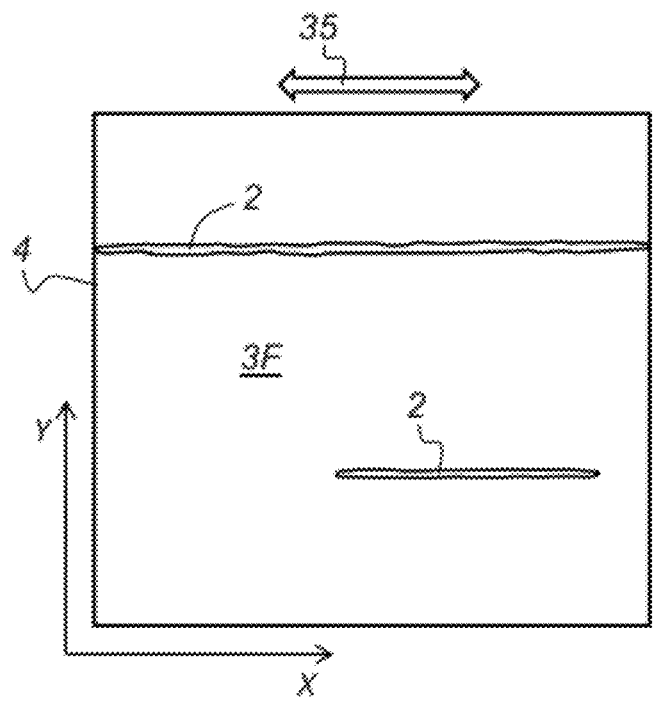
FIG. 5 shows a schematic top view of a wafer used for solar cells, wherein the wafer has the shape of a rectangle.

FIG. 5 shows a schematic top view of a wafer 4 used for solar cells, wherein wafer 4 has the shape of a rectangle. As mentioned above, wafer 4 is sawed-off from a silicon ingot. Since the form of the silicon ingot is a cuboid, the wafer 4 is rectangular. The saw marks 2 on the front side 3F of wafer 4 are oriented along a direction 35 of the saw.

Figure 6:
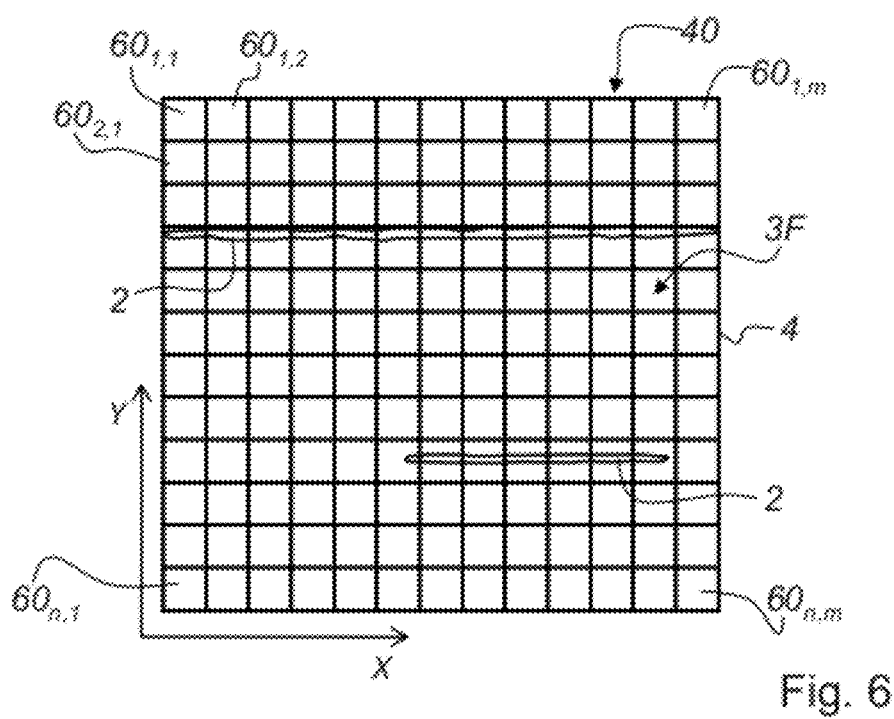
FIG. 6 shows a schematic view of the image of the wafer which is registered by pixels of the image sensor of the camera, wherein an field of view of the camera captures the entire surface of the wafer.

FIG. 6 shows a schematic view of an image 40 of the wafer 4 according to FIG. 5. Wafer 4 is registered by pixels $60_{n,m}$ of an image sensor of camera 6, wherein the field of view 7 of camera 6 captures the entire surface, here the front side 3F, of wafer 4. The image sensor of camera 6 with the plurality of pixels $60_{n,m}$ is oriented with wafer 4 so that the saw grooves 2 are approximately parallel to the pixel rows n or the pixel columns m of the image sensor. Preferably, wafer 4 is oriented so that the sides of wafer 4 (rectangular wafer) are parallel to the X-direction and the Y-direction respectively.

The process how the images 40 of the surface 3 of the wafer 4 are captured is shown in FIGS. 7A, 7B, 8A, 8B 9A, and 9B. The first set of images 40 (see FIGS. 7A, 8A, and 9A) is captured with the first line projector $8_1$ switched on. The second set of images 40 (see FIGS. 7B, 8B, and 9B) is captured with the second line projector $8_2$ switched on. According to the embodiment shown here, first line projector $8_1$ and second line projector $8_2$ are arranged such that they both illuminate the front side 3F of wafer 4. The first line projector $8_1$ and the second line projector $8_2$ are switched on and off in an alternating manner. The first line projector $8_1$ projects a pattern 20 of lines 22 on the front side 3F of wafer 4 so that lines 22 are parallel to the X-direction. Second line projector $8_2$ projects a pattern 20 of lines 22 on the front side 3F of wafer 4 so that the lines 22 are parallel to the Y-direction.

Figure 7A:
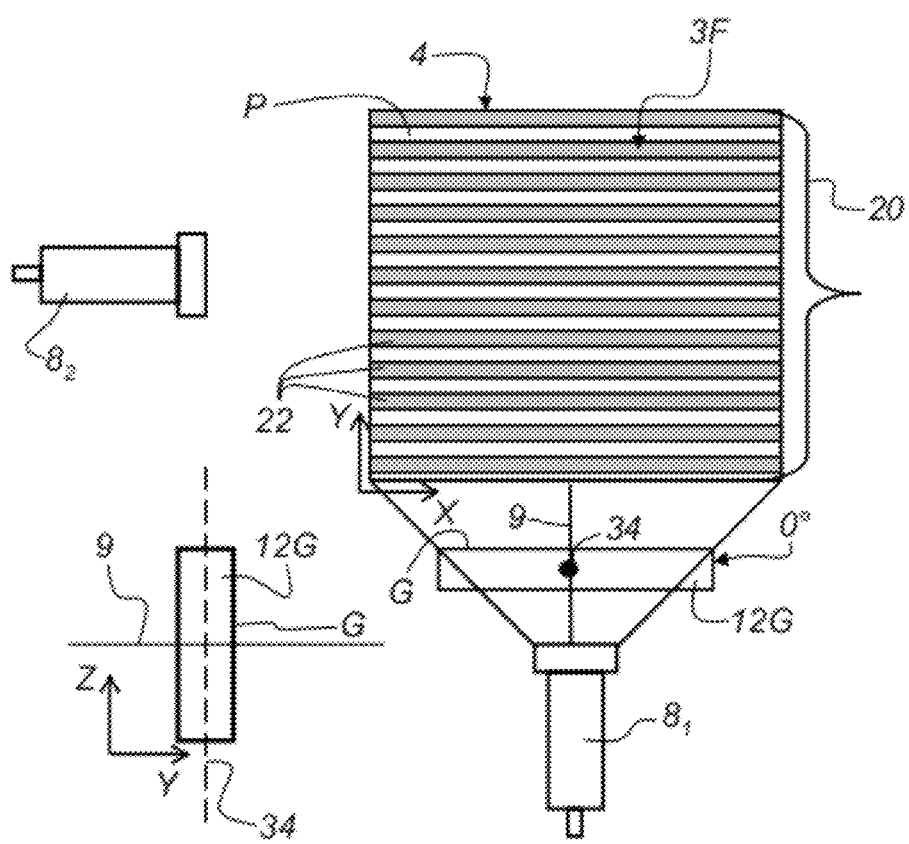
FIG. 7A shows the capture of an image of the front side surface of the wafer, a horizontal illumination pattern projected onto the wafer surface with a first line projector, and a glass plate in a first illumination light bundle, the glass plate being not tilted.
Figure 8A:
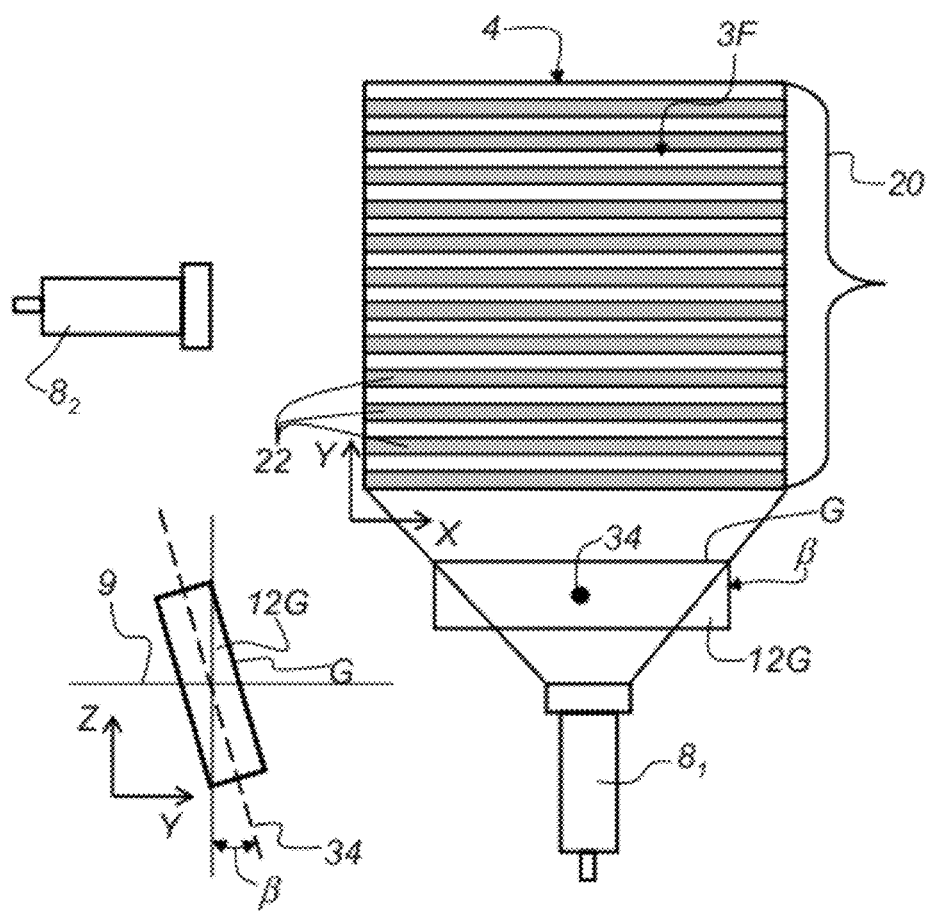
FIG. 8A shows the capture of an image of the front side surface of the wafer, a horizontal illumination pattern projected onto the wafer surface with the first line projector according to FIG. 7A, and the glass plate in a first illumination light bundle, the glass plate being tilted in the clockwise direction.
Figure 9A:
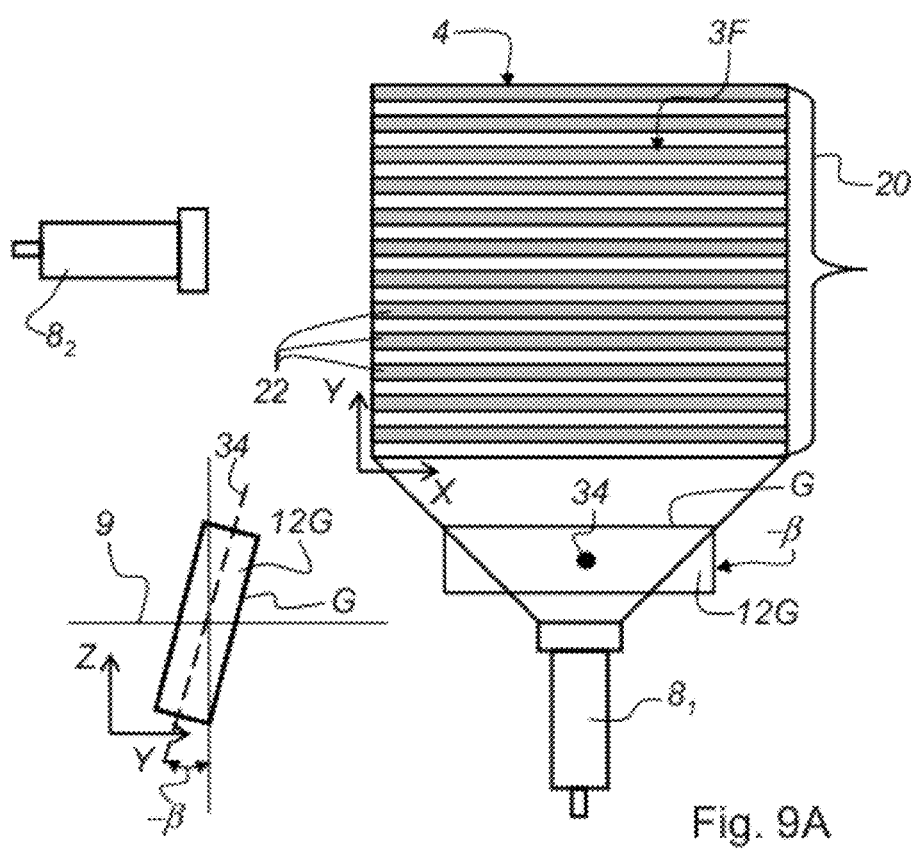
FIG. 9A shows the capture of an image of the front side surface of the wafer, a horizontal illumination pattern projected onto the wafer surface with the first line projector according to FIG. 7A, and the glass plate in the first illumination light bundle, the glass plate being tilted in the counter clockwise direction.

FIG. 7A shows the situation that the first line projector $8_1$ is switched on and projects a pattern 20 of lines 22 on front side 3F of wafer 4. The lines 22 are parallel to the X-direction. The tilt angle of the glass plate 120, placed in front of the first line projector $8_1$, is at 0° degrees, pictured in FIG. 7A wherein a rotation axis 34 (see side view) or a plane G of the glass plate 120 is perpendicular to the central beam axis 9. The image 40 of the entire front side 3F of wafer 4 is captured by camera 6. The next step in the acquisition of the set of images 40 is shown in FIG. 8A. The first line projector $8_1$ remains in the switched-on state and projects a pattern 20 of lines 22 on front side 3F of wafer 4. The lines 22 are parallel to the X-direction. The tilt angle of the glass plate 12G, placed in front of the first line projector $8_1$, is set to define value β unequal to 0° degrees, pictured in FIG. 8A wherein the rotation axis 34 (see side view) or a plane G of the glass plate 12G is tilted with respect to the central beam axis 9. Pattern 20 of lines 22 is shifted a defined distance on front side 3F wafer 4 and camera 6 captures an image 40 of the shifted pattern 20 of lines 22. FIG. 9A shows the situation that the tilt angle of the glass plate 12G, placed in front of the first line projector $8_1$, is set to defined value −β, pictured in FIG. 9A wherein the rotation axis 34 (see side view) or a plane G of the glass plate 12G is tilted with respect to the central beam axis 9. The first line projector $8_1$ remains in the switched-on state and projects a pattern 20 of lines 22 on front side 3F of wafer 4. The lines 22 are parallel to the X-direction and the image 40 is captured by camera 6.

Figure 7B:
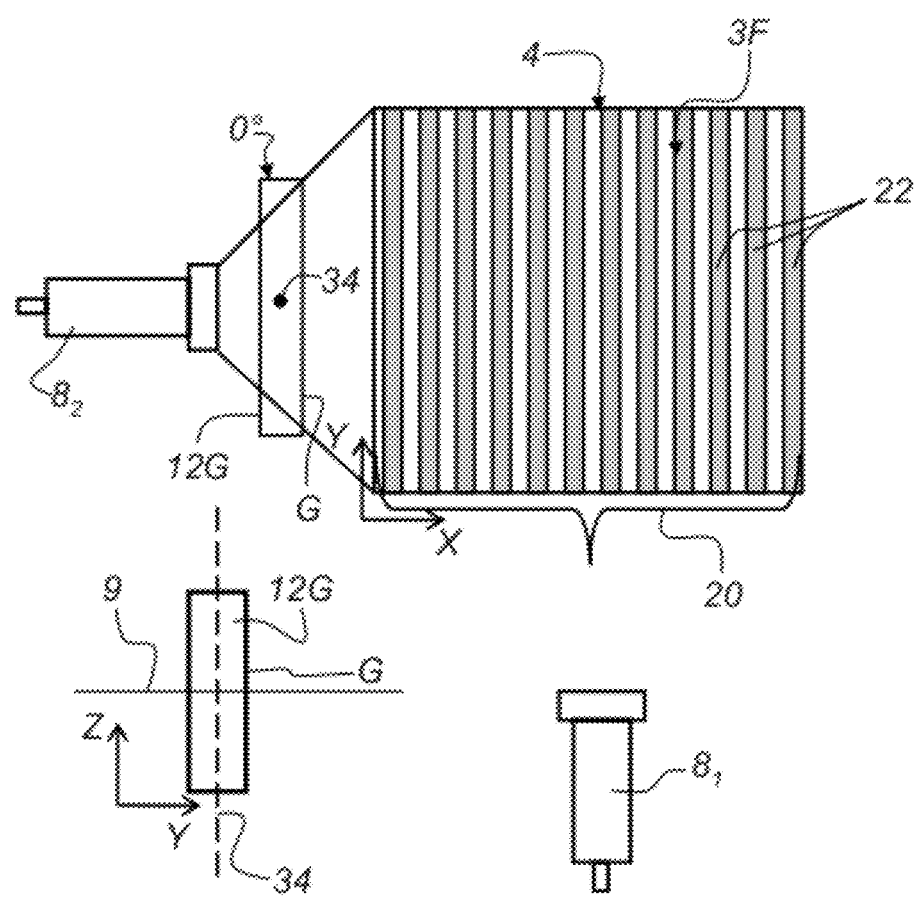
FIG. 7B shows the capture of an image of the front side surface of the wafer, a vertical illumination pattern projected onto the wafer surface with a second line projector, and a glass plate in a second illumination light bundle, the glass plate being not tilted.
Figure 8B:
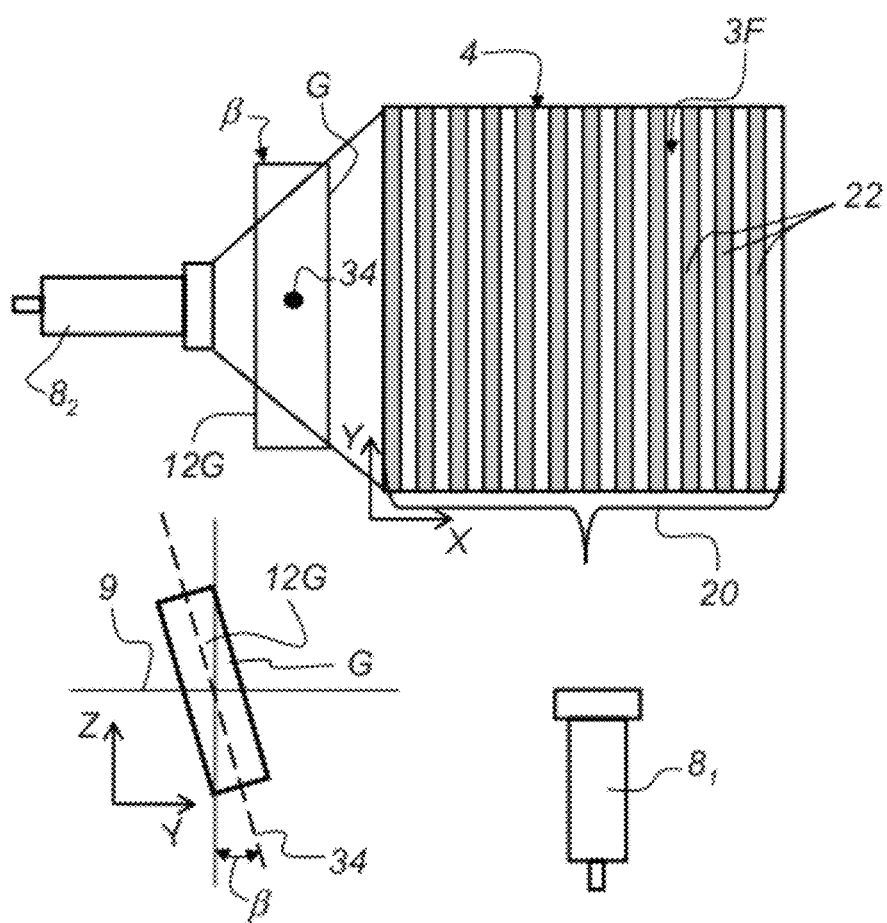
FIG. 8B shows the capture of an image of the front side surface of the wafer, a vertical illumination pattern projected onto the wafer surface with the second line projector according to FIG. 7B, and the glass plate in the second illumination light bundle, the glass plate being tilted in the clockwise direction.
Figure 9B:
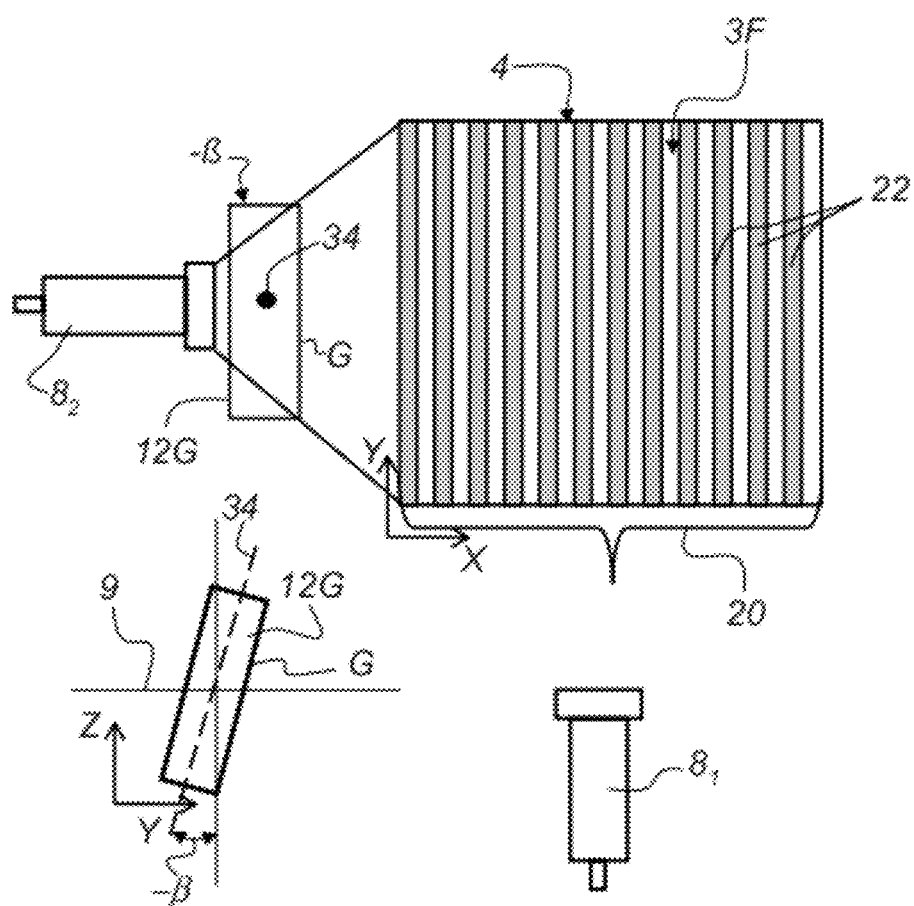
FIG. 9B shows the capture of an image of the front side surface of the wafer, a vertical illumination pattern projected onto the wafer surface with the second line projector according to FIG. 7B, and the glass plate in the second illumination light bundle, the glass plate being tilted in the counter clockwise direction.

FIG. 7B shows the situation that second line projector $8_2$ is switched on and projects a pattern 20 of lines 22 on front side 3F of wafer 4. The lines 22 are parallel to the Y-direction. The tilt angle of the glass plate 12G, placed in front of the second line projector $8_2$, is at 0° degrees, pictured in FIG. 7B by a center line 34 being positioned in the middle of glass plate 12G. The image 40 of the entire front side 3F of wafer 4 is captured by camera 6, The next step of the acquisition of the set of images 40 is shown in FIG. 8B. Second line projector $8_2$ remains in the switched-on state and projects a pattern 20 of lines 22 on front side 3F of wafer 4. The lines 22 are parallel to the Y-direction. The tilt angle of the glass plate 12G, placed in front of the second line projector $8_2$, is set to defined value β unequal to 0° degrees, pictured in FIG. 8B by a center line 34 being positioned leftward from the middle of glass plate 12G. The pattern 20 of lines 22 is shifted a defined distance on front side 3F of wafer 4 and camera 6 captures an image 40 of the shifted pattern 20 of lines 22. FIG. 9B shows the situation that the tilt angle of the glass plate 12G, placed in front of the second line projector $8_2$, is set to defined value −β, pictured in FIG. 9B by a center line 34 being positioned rightward from the middle of glass plate 12G.

FIGS. 7A, 7B, 8A, 8B, 9A, and 9B show that the set of images 40, wherein the lines 22 are parallel to the X-direction, comprises three images 40 and the set of images 40, wherein the lines 22 are parallel to the Y-direction, comprises three images 40 as well. The amount of shift is controlled by the amount of rotation or tilt of the respective glass plate 12G in front of first line projector $8_1$ and second line projector $8_2$ respectively. The images 40 of each set are taken with the lines 22 shifted by a defined amount which is zero, one-third and two third of the line period, in particular, in FIG. 7A, 7B the lines 22 are not shifted (tilt angle of glass plate 12G is 0°), in FIG. 8A, 8B the lines 22 are shifted wherein the tilt angle of the glass plate 12G is β, and in FIG. 9A, 9B the lines 22 are shifted wherein the tilt angle of the glass plate 12G is −β. In any case, the amount of the stepwise shift of lines 22 is set to a degree that the entire surface 3 of wafer 4 is covered. It is obvious for a skilled person in the art that the amount of images 40 taken per set is not limited to three images 40.

Figure 10:
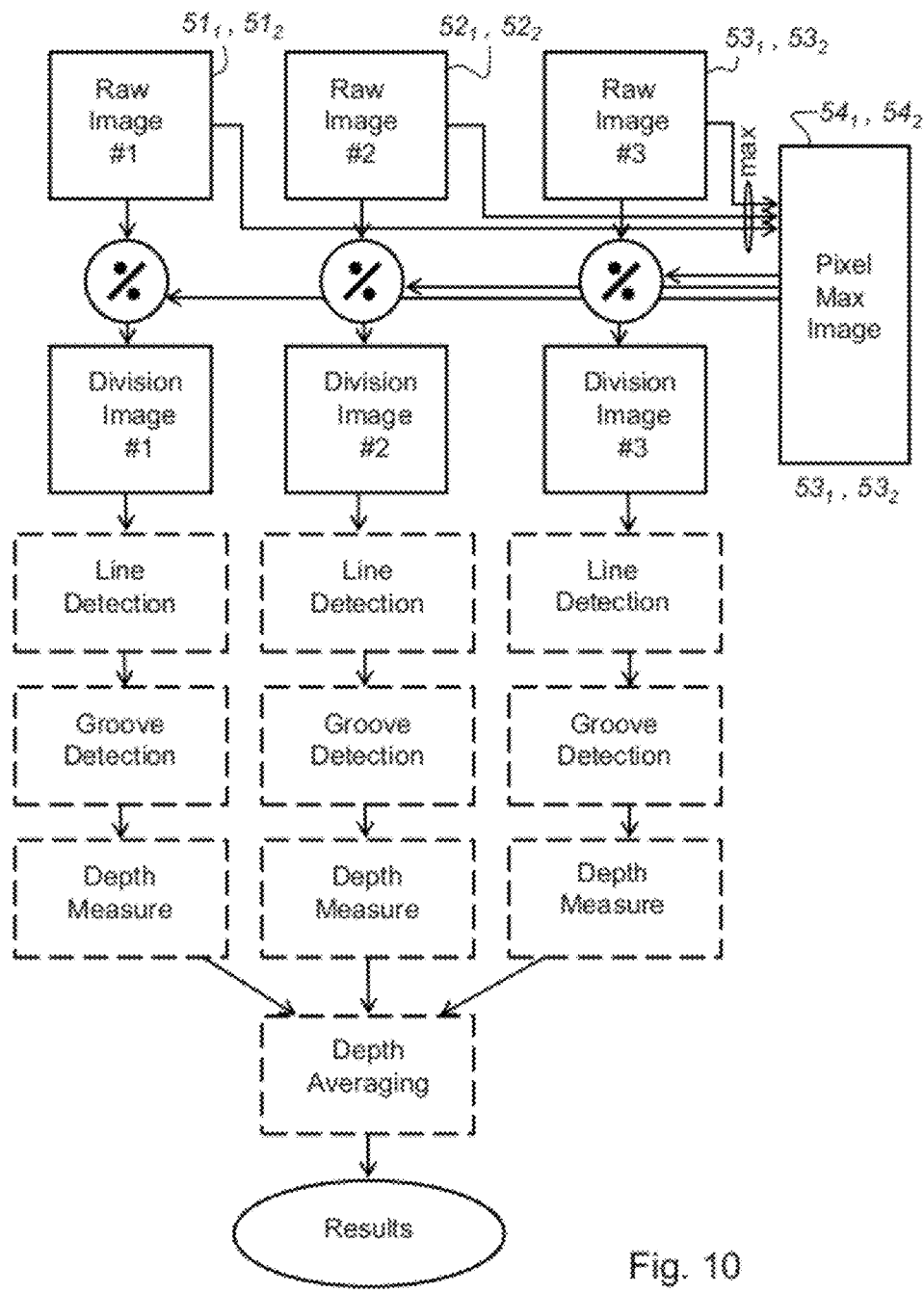
FIG. 10 shows a schematic flow chart of the inventive method to detect saw marks oriented in both directions on the surface of a wafer.

FIG. 10 shows a schematic flow chart of the inventive method to detect saw marks 2 on the surface 3 of a wafer 4. As shown in FIGS. 7A, 7B, 8A, 8B, 9A, and 9B a first line projector $8_1$ and a second line projector $8_2$ are arranged to illuminate the front side 3F of wafer 4. The first line projector $8_1$ and the second line projector $8_2$ are positioned such that their respective central beam axes 9 are perpendicular to each other. Initially, first line projector $8_1$ projects a first pattern 20 of lines 22 of a first orientation (parallel to the X-direction) onto the at least one surface 3 of wafer 4. A first raw image 51, a second raw image 52 and a third raw image 53 are captured, wherein for each raw image $51_1, 52_1, 53_1$ of the first pattern 20 of lines 22 the lines 22 are shifted a definite distance perpendicular to the orientation of the first pattern 20 of lines 22. The same is done with a second set of raw images $51_2, 52_2, 53_2$ of a second pattern 20 of lines 22, wherein the lines 22 are oriented parallel to the Y-direction.

After the raw images $51_1, 52_1, 53_1$ and $51_2, 52_2, 53_2$ of each set are captured, the multiple raw images $51_1, 52_1, 53_1$ and $51_2, 52_2, 53_2$ in each orientation are combined to improve the quality of each image and to remove unwanted artifacts. A reference image $54_1, 54_2$ is computed, wherein the pixel values of the first reference image $54_1$ are maximum pixel values of the first set of raw images $51_1, 52_1, 53_1$. Analogously, a second reference image $54_2$ is computed, wherein the pixel values of the second reference image $54_2$ are maximum pixel values of the second set of raw images $51_2, 52_2, 53_2$. In the next step each image of the first set of raw images $51_1$, $52_1$, $53_1$ and each image of the second set of raw images $51_2$, $52_2$, $53_2$ is divided by the first reference image $54_1$ and the second reference image $54_2$ respectively. The first set of raw images $51_1$, $52_1$, $53_1$ and the second set of raw images $51_2$, $52_2$, $53_2$ are numerically resealed which is done by multiplying them with a constant value in order to obtain the same range of values (for example 0-255) as the original images have.

In the next process step, candidate grooves (saw grooves 2) are detected in all improved images. Assuming, without any loss of generality, that the projected lines are approximately horizontal in the image, the groove detection is achieved by a variety of steps. Firstly, a detection of a location of the projected lines 22 is carried out in each column of pixels $60_{n,m}$. Secondly, each line 22 is tracked horizontally and local deviations from a straight line are computed. Thirdly, a Hough transformation is carried out with positions of a straight line where the local deviation is above a threshold. Fourthly, peaks are searched for in the Hough transformation, which correspond to the position and orientation of detected grooves 2.

According to a further embodiment of the invention the raw images #1, #2 and #3 are combined into one single image of improved quality. That is done by a process known as "phase shift extraction" that compares the intensity of the three images $51_1$, $52_1$, $53_1$ at each pixel location. The combined image is known as a "phase image". The grooves are detected and measured in the phase image. The nature of the phase image is such that phase jumps (from −pi to +pi or from +pi to −pi) must be taken into account ("unwrapped") when line fits and deviations are computed.

In next step, the depths of the detected grooves 2 in all improved images are measured. For each candidate groove 2 detected, a high and low point of a groove profile are computed along each direction of a detected groove 2. The computation starts from the tracked line positions. The high points and low points are tracked across adjacent directions or lines. A local depth of detected grooves 2 is estimated by means of curve fittings through line positions near the high and low points. An average depth of the grooves is estimated in pixels over a certain length along the groove 2 by means of a moving average. Finally, the depth of the groove 2 is translated from pixels to microns by means of pre-computed calibration parameters.

In a next step, the depth of the grooves 2 is averaged, which is achieved by an averaged depth profile computed in three dimensions over the improved set of first images $51_1$, $52_1$, $53_1$ and set of second images $51_2$, $52_2$, $53_2$. At the end, the location and depth of the grooves 2 are reported. A file is written, from which file the location and the depth of the grooves 2 can be retrieved by a line engineer. The location and the depth of the deepest saw groove 2 on the surface 3 of wafer 4 is retrievable from the file as well.

The invention has been described with reference to preferred embodiments. However, it is obvious for a person skilled in the art that modifications and alterations of the invention can be made without leaving the scope of the subsequent claims.

REFERENCE NUMERALS 1 apparatus
2 saw mark; saw groove
3 surface
3B back side of wafer
3F front side of wafer
4 wafer
5 light bundle
6, $6_1$, $6_2$ camera
7 field of view
8 line projector
$8_1$ first line projector
$8_2$ second line projector
$8_3$ third line projector
$8_4$ fourth line projector
9 central beam axis
10 light source
11 motor
12 line shifter
12G glass plate
14 frame grabber
15 optical system
16 image processor
18 patterned glass plates
19 propagation direction
20 pattern
22 lines
24 exit lens
26 condenser lenses; condenser system
27 first glass plate
28 second glass plate
30 light guide
32 moving means
34 rotation axis
35 direction of saw
40 image of the wafer
$51_1$, $51_2$ first raw image
$52_1$, $52_2$ second raw image
$53_1$, $53_2$ third raw image
$54_1$, $54_2$ reference image
$60_{n,m}$ pixels of image sensor of camera
G plane of glass plate
P plane of wafer
X X-direction
Y Y-direction
α acute angle
β tilt angle

What is claimed is:

1. An apparatus for inspection comprising:
   at least one camera defining a field of view, wherein the field of view is configured such that at least a portion of a surface of the wafer is captured;
   at least one light source;
   at least one line projector configured to provide a light bundle centered about a central beam axis, wherein the at least one line projector is arranged such that the central beam axis is oriented at an acute angle with respect to a plane of the wafer, wherein the at least one light source is configured to provide light to the at least one line projector, wherein the at least one line projector is configured to project a pattern of a plurality of lines onto at least one of a front side or a back side of the wafer;
   at least one line shifter positioned in the light bundle between the at least one line projector and the surface of the wafer;
   a frame grabber; and
   an image processor, wherein image capture of the at least one of the front side or the back side of the wafer is synchronized by the frame grabber in coordination with the position of the pattern of lines on the at least one of the front side of the wafer or the back side of the wafer, wherein the image processor is configured to perform a three-dimensional inspection of one or more saw marks of the wafer.

2. The apparatus of claim 1, wherein the at least one line projector and the surface of the wafer are positionable with respect to each other such that the at least one line projector projects a first and a second pattern of lines onto the surface of the wafer, wherein the first pattern of lines is oriented at an angle with respect to the second pattern of lines.

3. The apparatus of claim 2, wherein the lines of the first pattern of lines are perpendicular to the lines of the second pattern of lines.

4. The apparatus of claim 1, wherein the at least one line shifter includes a glass plate connected to a motor for rotating the glass plate such that at least one of the first pattern of lines or the second pattern of lines is shifted on the surface of the wafer.

5. The apparatus of claim 1, wherein the at least one line shifter includes a plurality of glass plates, at least some of the glass plates being arranged at different angles in a positioner, the positioner being drivable by a motor in order to position a glass plate of a different tilt angle into the light bundle such that at least one of the first pattern of lines or the second pattern of lines is shifted on the surface of the wafer.

6. The apparatus of claim 1, wherein the at least one line projector includes at least two patterned glass plates with a pattern of lines arranged between an exit lens and a condenser system, wherein a first glass plate has a variable-pitch Ronchi ruling in order to compensate for a perspective effect and to project a uniform pattern of lines onto the surface of the wafer, wherein a second glass plate includes a variable transmittance pattern to compensate for a perspective effect and to project the uniform pattern of lines onto the surface of the wafer.

7. The apparatus of claim 1, wherein the at least one light source is directly optically coupled to the at least one line projector.

8. The apparatus of claim 7, wherein the at least one light source comprises one or more LEDs.

9. The apparatus of claim 1, wherein the at least one light source is optically coupled to the at least one line projector via a light guide.

10. The apparatus of claim 9, wherein the at least one light source comprises one or more LEDs.

11. The apparatus of claim 1, wherein the least one camera is communicatively coupled to the frame grabber and the image processor such that a motion of the at least one line shifter, a switching of the at least one light source and a capture of an image of the surface of the wafer at different positions of the pattern of lines on the surface of the wafer are synchronized by the frame grabber.

12. A method of inspection comprising:
projecting a first pattern of lines of a first orientation onto at least one surface of a wafer;
capturing a first set of first images of the at least one surface of the wafer, wherein lines of the first pattern of lines of at least some images of the first pattern of lines are shifted a definite distance perpendicular to the orientation of the first pattern of lines;
projecting a second pattern of lines of a second orientation onto the at least one surface of the wafer;
capturing a second set of second images of the at least one surface of the wafer, wherein lines of the second pattern of lines of at least some images of the second pattern of lines are shifted a definite distance perpendicular to the second orientation of the second pattern of lines;
generating a combined first image from the set of first images;
generating a combined second image from the set of second images;
computing an improved set of first images from the combined first image and an improved set of second images from the combined second image;
detecting grooves in at least one of the improved set of first images and/or in at least one of the improved set of second images;
measuring a depth of a detected groove in at least some of the improved set of first images;
measuring a depth of a detected groove in at least some of the improved set of second images;
averaging the depth of at least some grooves across the at least some of the improved set of first images or the at least some of the improved set of second images; and
recording the depth, location and the orientation of the detected grooves on the at least one surface of the wafer to perform a three-dimensional inspection of one or more saw marks of the wafer.

13. The method of claim 12, wherein the combined first image and the combined second image comprises:
computing a first reference image, wherein pixel values of the first reference image are maximum pixel values of the first set of images;
computing a second reference image, wherein pixel values of the second reference image are maximum pixel values of the second set of images;
dividing at least some of the first set of images by the first reference image;
dividing at least some of the second set of images by the second reference image; and
numerically rescaling the first set of images and the second set of images.

14. The method of claim 12, wherein detecting grooves in at least one of the improved set of first images and/or in at least one of the improved set of second images comprises:
detecting a location of the projected lines in each column of pixels in at least one of the improved set of first images and/or in at least one of the improved set of second images;
tracking the location of the projected lines along a specific direction;
computing one or more local deviations from a straight line along the specific direction;
carrying out a transformation with positions of a straight line, wherein the one or more local deviations are above a threshold; and
finding peaks in the transformation corresponding to at least one of position or orientation of detected grooves.

15. The method of claim 12, wherein: at least one of the measuring a depth of a detected groove in at least some of the improved set of first images or the measuring a depth of a detected groove in at least some of the improved set of second images comprises:
computing for each detected groove a high and low point of a groove profile along each direction of a detected groove;
tracking high points and low points across adjacent directions;
estimating a local depth of detected grooves utilizing one or more curve fittings along line positions proximate to the high and low points; and
estimating an average depth of the grooves over a length along the groove utilizing a moving average.

16. The method of claim 12, wherein the averaging the depth of at least some grooves across the at least some of the improved set of first images or the at least some of the improved set of second images comprises:

averaging a depth profile computed in three dimensions over at least one of the improved set of images or the improved set of second images.

17. An apparatus for inspection comprising:
at least one camera defining a field of view, the at least one camera arranged substantially perpendicular to a plane of a wafer, wherein the field of view is configured such that an entire surface of the wafer is captured;
at least one light source;
a first line projector configured to provide a first light bundle centered about a central beam axis, wherein the first line projector is arranged such that the central beam axis is oriented at an acute angle with respect to the plane of the wafer, wherein the at least one light source is configured to provide light to the first line projector, wherein the first line projector is configured to project a first pattern of a plurality of lines having a first orientation onto at least one of a front side of the wafer or a back side of the wafer;
a second line projector configured to provide a second light bundle centered about a central beam axis, wherein the second line projector is arranged such that the central beam axis is oriented at an acute angle with respect to the plane of the wafer, wherein the at least one light source is configured to provide light to the second line projector, wherein the second line projector is configured to project a second pattern of a plurality of lines having a second orientation onto at least one of the front side of the wafer or the back side of the wafer;
a first line shifter positioned in the first light bundle between the first line projector and the first surface of the wafer;
a second line shifter positioned in the second light bundle between the second line prosection and the second surface of the wafer;
frame grabber; and
an image processor, wherein image capture of at least one of the front side of the wafer or the back side of the wafer is synchronized by the frame grabber in coordination with the position of at least one of the first pattern of a plurality of lines or the second pattern of a plurality of lines on at least one of the front side of the wafer or the back side of the wafer, wherein the image processor is configured to perform a three-dimensional inspection of one or more saw marks of the wafer.

18. The apparatus of claim 17, wherein the first pattern of plurality of lines is perpendicular to the second pattern of plurality of lines.

19. The apparatus of claim 17, wherein at least one of the first line shifter or the second line shifter includes a glass plate connected to a motor for rotating the glass plate such that the at least one of the first pattern of a plurality of lines or the second pattern of a plurality of lines is shifted on at least one of the first surface of the wafer or the second surface of the wafer.

20. The apparatus of claim 17, wherein at least one of the first line shifter or the second line shifter includes a plurality of glass plates, where at least some glass plates are arranged at different angles in a positioner, the positioner being drivable by a motor in order to position a glass plate of a different tilt angle into at least one of the first light bundle of the first line projector or the second light bundle of the second line projector such that at least one of the first pattern of a plurality of lines of the second pattern of a plurality of lines is shifted on at least one of the first surface of the wafer or the second surface of the wafer in at least one of an X-direction or a Y-direction.

21. The apparatus of claim 17, wherein at least one of the first line projector or the second line projector includes two patterned glass plates, each of the two patterned glass plates having a pattern of lines arranged between an exit lens and a condenser system, wherein a first glass plate has a variable-pitch Ronchi ruling in order to compensate for a perspective effect and to project uniform pattern of lines onto at least one of the first surface of the wafer or at least one of the second surface of the wafer, wherein the second glass plate has a variable transmittance pattern to compensate for a perspective effect and to project uniform pattern lines onto at least one of the first surface of the wafer or at least one of the second surface of the wafer.

22. The apparatus of claim 17, wherein the at least one camera is communicatively coupled to the frame grabber and the image processor such that a motion of at least one of the first line shifter or the second line shifter, a switching of the at least one light source and a capture of an image of the surface of the wafer produced by the first line projector and the second line projector are synchronized by the frame grabber.

23. An apparatus for inspection comprising:
at least one camera defining a field of view, wherein the at least one camera is arranged perpendicular to a plane of the wafer, wherein the field of view is configured such that an entire surface of the wafer is captured;
at least one light source;
at least one line projector configured to provide a light bundle centered about a central beam axis, wherein the at least one line projector is arranged such that the central beam axis is oriented at an acute angle with respect to the plane of the wafer, wherein the at least one line projector is configured to project a first pattern of a plurality of lines with a first orientation onto the surface of the wafer;
at least one line shifter positioned in the light bundle between the at least one line projector and the surface of the wafer;
moving means for providing a relative rotation between the wafer and the at least one line projector to maintain the acute angle of the line projector with regard to the plane of the wafer in order to project a second pattern of a plurality of lines with a second orientation onto the surface of the wafer;
a frame grabber; and
an image processor, wherein image capture of at least one of the first pattern of lines or the second pattern of lines projected onto the surface of the wafer is synchronized by the frame grabber in coordination with the position of the at least one line shifter in the light bundle and the relative rotational position of the wafer and the at least one line projector, wherein the image processor is configured to perform a three-dimensional inspection of one or more saw marks of the wafer.

24. An apparatus for inspection comprising:
at least two cameras, each camera defining a field of view, each camera arranged perpendicular to a plane of at least one of a front side of the wafer or the back side of the wafer, wherein the field of view of the at least two cameras is configured such that at least one of an entire front side of the wafer or an entire back side of the wafer is captured;
at least one light source;
a first line projector configured to provide a first light bundle centered about a central beam axis, wherein the first line projector is arranged such that the central beam axis is at an acute angle with respect to the plane and the front side of the wafer;

a second line projector configured to provide a second light bundle centered about a central beam axis, wherein the second line projector is arranged such that the central beam axis is at an acute angle with respect to the plane and the back side of the wafer, wherein the at least one light source is configured to provide light to at least one of the first line projector or the second line projector, wherein at least one of the first line projector or the second line project are configured to project a pattern of a plurality of lines onto at least one of a front side or a back side of the wafer;

at least one line shifter positioned in at least one of the first light bundle or the second light bundle between the at least one of the first line projector or the second line protector and the surface of the wafer;

a frame grabber; and an image processor, wherein image capture of at least one of the front side of the wafer or the back side of the wafer is synchronized by the frame grabber in coordination with the position of the pattern of lines on the at least one of a front side or a back side of the wafer, wherein the image processor is configured to perform a three-dimensional inspection of one or more saw marks of the wafer.

25. The apparatus of claim 24, wherein the moving means provides a relative rotation between the wafer and the at least one line projector to maintain the acute angle of the at least one line projector with respect to the plane of the wafer in order to project a second pattern of a plurality of lines with a second orientation onto the surface of the wafer, wherein the frame grabber and the image processor synchronize the image capture of the first pattern of lines and the second pattern of lines projected onto the at least one of a front side of the wafer or a back side of the wafer, the position of the at least one line shifter in the light bundle and the relative rotational position of the wafer and the first line projector and second line projector with respect to each other.

26. An apparatus for inspection wafer comprising:

at least one camera defining a field of view, wherein the field of view is configured such that at least a portion of a surface of a wafer is captured, wherein the wafer and camera are arranged such that one or more saw marks of the wafer have a defined orientation in the field of view of the camera;

at least one light source;

at least one line projector configured to provide a light bundle centered about a central beam axis, wherein the at least one line projector is arranged such that the central beam axis is oriented at an acute angle with respect to a plane of the wafer, wherein the at least one light source is configured to provide light to the at least one line projector, wherein the at least one line projector is configured to project a pattern of a plurality of lines onto at least one of a front side of the wafer or a back side of the wafer;

at least one line shifter positioned in the light bundle between the at least one line projector and the surface of the wafer;

a frame grabber; and an image processor, wherein image capture of the at least one of the front side of the wafer or the back side of the wafer is synchronized by the frame grabber in coordination with the position of the pattern of lines on the at least one of the front side of the wafer or the back side of the wafer, wherein the image processor is configured to perform a three-dimensional inspection of the one or more saw marks of the wafer.

27. A method of inspection comprising:

determining an orientation of one or more saw marks on a wafer;

providing at least one line projector;

projecting a first pattern of lines of a first orientation onto at least one surface of the wafer, wherein the first pattern of lines is oriented at an angle with respect to the one or more saw marks;

capturing a set of first images of the at least one surface of the wafer, wherein one or more lines of the first pattern of lines of at least some images are shifted a definite distance perpendicular to the orientation of the first pattern of lines;

generating a combined first image from the set of first images;

computing an improved set of first images from the combined first image;

detecting grooves in at least one of the improved set of first images;

measuring a depth of a detected groove in at least some of the improved set of first images;

averaging the depth of at least some grooves across the at least some of the improved set of first images; and recording at least one of the depth, location or the orientation of the detected grooves on the at least one surface of the wafer to perform a three-dimensional inspection of one or more saw marks of the wafer.

28. The method of claim 27, further comprising: performing a rotation between the wafer and the at least one line projector such that the orientation of the one or more saw marks on the wafer is non-parallel with the first pattern of lines.

\* \* \* \* \*